US007666282B2

(12) United States Patent
Sylvester et al.

(10) Patent No.: US 7,666,282 B2
(45) Date of Patent: Feb. 23, 2010

(54) PROCESS FOR PROVIDING ETHANOL

(75) Inventors: Robert G. Sylvester, Newark, DE (US);
Stephen Thomas Breske, Wilmington, DE (US); David A. Culver, Salem, NJ (US); Bruce M. Vrana, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 669 days.

(21) Appl. No.: 11/320,206

(22) Filed: Dec. 28, 2005

(65) Prior Publication Data

US 2007/0144886 A1    Jun. 28, 2007

(51) Int. Cl.
| B01D 3/06 | (2006.01) |
| B01D 3/10 | (2006.01) |
| B01D 3/14 | (2006.01) |
| C07C 31/08 | (2006.01) |
| C07C 29/80 | (2006.01) |

(52) U.S. Cl. .............................. 203/19; 203/41; 203/73; 203/87; 203/88; 203/91; 210/664; 426/494; 435/161; 568/913; 568/916

(58) Field of Classification Search ............ 203/18–19, 203/39–41, 73, 87–88, 91; 210/664; 426/11, 426/493, 494; 435/161; 568/913, 916
See application file for complete search history.

(56) References Cited

U.S. PATENT DOCUMENTS

| 4,217,178 A | * | 8/1980 | Katzen et al. ................ 203/19 |
| 4,422,903 A | * | 12/1983 | Messick et al. ............... 203/19 |
| 4,568,356 A | | 2/1986 | Chambers |
| 4,867,997 A | * | 9/1989 | Wiesenberger et al. ....... 426/387 |
| 4,983,304 A | | 1/1991 | Tsugita et al. |
| 5,955,135 A | * | 9/1999 | Boucher et al. .............. 426/492 |
| 7,297,236 B1 | * | 11/2007 | Vander Griend ............. 202/153 |

FOREIGN PATENT DOCUMENTS

| BR | 8703445 A1 | 1/1989 |
| RO | 112503 B | 11/1993 |
| WO | WO 2004/088230 A2 | 10/2004 |

OTHER PUBLICATIONS

Aden et al., Lignocellulosic Biomass to Ethanol Process Design and Economics Utilizing Co-Current Dilute ACD Prehydrolysis and Enzymatic Hydrolysis for Corn Stover, NREL Report No. TP-510-32438, Section II.5, p. 36-39.

P. W. Madson et al., Fuel Ethanol Production in Fuel Alcohol Textbook, Alltech Inc., 1999, Chapter 17, pp. 257-268.

(Continued)

*Primary Examiner*—Virginia Manoharan

(57) ABSTRACT

The invention is a process for the purification of ethanol. In one embodiment the process includes boiling a degassed beer feed (106) in a pre-boiler (110) to provide a vapor by-pass fraction (112) that by-passes the conventional beer column and is fed into the rectifier column (124). The process allows free capacity in the rectifier column of new or established plants to be filled by ethanol-water vapor and/or condensate streams that do not originate from the beer column.

13 Claims, 8 Drawing Sheets

OTHER PUBLICATIONS

D. R. Garg et al., Molecular Sieve Dehydration Cycle for High Water Content Streams, CEP, Apr. 1983, pp. 60-65.

Michael R. Ladisch et al., Cornmeal Adsorber for Dehydrating Ethanol Vapors, I&EC Process Design & Development, 1984, vol. 23:437.

S. Skouras et al., Time (Energy) Requirements in Closed Batch Distillation Arrangements, Computers & Chemical Engineering, vol. 28:829-837, 2004.

* cited by examiner (Conventional Process - Prior Art)

(Conventional Process - Prior Art)

PROCESS FOR PROVIDING ETHANOL

STATEMENT OF GOVERNMENT RIGHTS

This invention was made with support by the United States government and the government has certain rights in the invention.

FIELD OF INVENTION

The invention relates to processes for making motor fuel grade ethanol.

BACKGROUND OF INVENTION

Ethanol is an important source of energy and useful as an alternative to petroleum based gasoline and diesel products. Ethanol is produced by fermentation of a wide variety of organic feedstocks to provide a beer that is distilled and dehydrated to produce a high purity product. Aden, et al, in "Lignocellulosic Biomass to Ethanol Process Design and Economics Utilizing Co-Current Dilute Acid Prehydrolysis and Enzymatic Hydrolysis for Corn Stover", NREL Report No. TP-510-32438; and Madson, P. W. and D. A. Monceaux, (Fuel Ethanol Production), in "Fuel Alcohol Textbook" Alltech Inc., 1999; provide an overview of the process. Substantial capital investment and energy are required to concentrate ethanol from a beer concentration of about 6 to about 16 wt % ethanol in water to a minimum of 99.5 wt % ethanol used in fuel grade ethanol. The concentration process operates through the ethanol-water azeotrope of about 95 wt % ethanol that has to be further dehydrated. In a typical fuel ethanol plant, the ethanol is first distilled from beer in a column, known as the beer column, designed to recover almost all ethanol from the spent beer. Vapor from this column passes to a second column, the rectifier column, wherein ethanol is concentrated to about 92 wt % ethanol, the substantial portion of the remainder being water. The vapor from the rectifier column is further dehydrated by passing it through a bed of a dehydration agent to provide the required 99.5 wt % ethanol vapor stream. Typically the dehydration agent is a 3 A molecular sieve material, however other dehydration agents such as corn grits, for instance, can be used. When the bed of dehydration agent is spent, it is taken off line and regenerated to provide an active dehydration bed and an ethanol-water vapor or liquid stream that is typically recycled to the rectifier column.

This latter dehydration process has attracted much attention of scientists and engineers because it is a critical and expensive step in the refining process. Typical plants now use 3 A molecular sieve beds as the dehydration agent. Molecular sieves adsorb water, in this case from an ethanol vapor, and must be regenerated as the sieve becomes saturated. One way to do this is to pass very hot, dry gas through the bed. The fuel ethanol industry found that under the conditions of ethanol dehydration, the hot gas caused the molecular sieves to crumble (Madson, 1999). Instead, they began to regenerate the bed with 99.5 wt % ethanol vapor available at the desired temperature from a parallel molecular sieve bed. They also learned to retain the heat of adsorption in the bed (Garg, D. R. and J. P. Ausikaitis, "Molecular Sieve Dehydration Cycle for High Water Content Streams", CEP, April 1983, p 60-65) so that the countercurrent flow of ethanol vapor could regenerate the bed with little or no heat addition (Aden, 2002). But a problem created by this approach is that the ethanol vapor used in regeneration is contaminated with water. This ethanol must be returned to the rectification section of the distillation equipment and redistilled to 92 wt % concentration. Thus, it is accepted, and most plants are designed for the fact, that a certain fraction of the capacity of the rectifier column will be taken by the regenerate stream of ethanol-water provided by the regeneration of the molecular sieve or other dehydration beds. However, because of the significant emphasis on the dehydration process, alternative processes have been developed to dehydrate the ethanol vapor stream that require less volumes to be recycled to the rectifier.

Brazilian patent, BR 8703445(A1), describes an alternative process for regenerating molecular sieve beds, wherein a hot inert gas such as carbon dioxide, is passed through the molecular sieve bed. Such a process is one example of a variety of processes that may have the potential to decrease the amount of ethanol being recycled to the rectifier column as a result of the dehydration process. Any improvement in the molecular sieve regeneration process that ultimately liberates capacity in the rectifier column may be advantageous. However, in many existing plants the beer column and rectifier columns are designed for equivalent capacities wherein the rectifier column is designed to have a predetermined fraction of capacity allocated for the ethanol-water. Increased capacity in the molecular sieve bed and/or rectifier would not eliminate the bottleneck of the beer column.

Needed is a process that allows free capacity in the rectifier column to be filled by alternative ethanol-water vapor and/or condensate streams from sources other than the existing beer column. Such a process would allow improvements in molecular sieve bed regeneration to be used in improving the overall throughput of existing and new plants.

SUMMARY OF INVENTION

One embodiment of the invention is a process for providing ethanol comprising: (a) flashing carbon dioxide from a beer stream (100) to provide a carbon dioxide gas stream (104) and a degassed beer feed (106); (b) boiling the degassed beer feed (106) in a pre-boiler to provide a vapor by-pass fraction (112) and a beer column feed stream (114); (c) distilling the beer column feed stream (114) in a beer column to provide an overhead vapor fraction (118) and a spent beer fraction (122); (d) distilling in a rectifier column (124), a combination comprising the vapor by-pass fraction (112) and the overhead vapor fraction (118) to provide an ethanol-rich rectifier overhead vapor stream (126) and a water-rich rectifier bottoms stream (128).

Another embodiment of the invention is a process for providing ethanol, comprising: (a) flashing and boiling from a beer stream comprising a liquid-solids fraction, carbon dioxide and about 2 to about 14 wt % of the liquid-solids fraction to provide a beer column feed stream (514) and a carbon dioxide-ethanol-water vapor fraction (500); (b) condensing the carbon dioxide-ethanol-water stream to provide a ethanol-water liquid stream (502) and a carbon dioxide gas stream (503); (c) distilling the beer column feed stream in a beer column to provide an overhead vapor fraction (518) and a spent beer fraction (522); and (d) distilling, in a rectifier column (124) a combination of the ethanol-water liquid stream (502) and the overhead vapor fraction (518) to provide an ethanol-rich rectifier overhead vapor stream (126) and a water-rich rectifier bottoms stream (128).

DETAILED DESCRIPTION OF INVENTION

Beer streams useful in the invention include any biomass beer streams derived from the fermentation of organic biomass in water. Typical beer streams include those produced in "dry grind" or "wet mill" fuel ethanol plants, using grain and/or grain by-products; sugar fermentation process, including sugar sources such as, sugar cane and sugar beads; and cellulose-to-ethanol plants, including lignocellulosics, such as, switch-grass, wood, hay, straw, stover, and bagasse. The beer stream typically contains carbon dioxide, ethanol, water, residual sugars, and biomass solids. Beer streams useful in the process of the invention include streams characterized by an ethanol-water mix of about 1 to about 20 wt % ethanol, and preferably, about 4 to about 16 wt % ethanol.

Figure 1A:
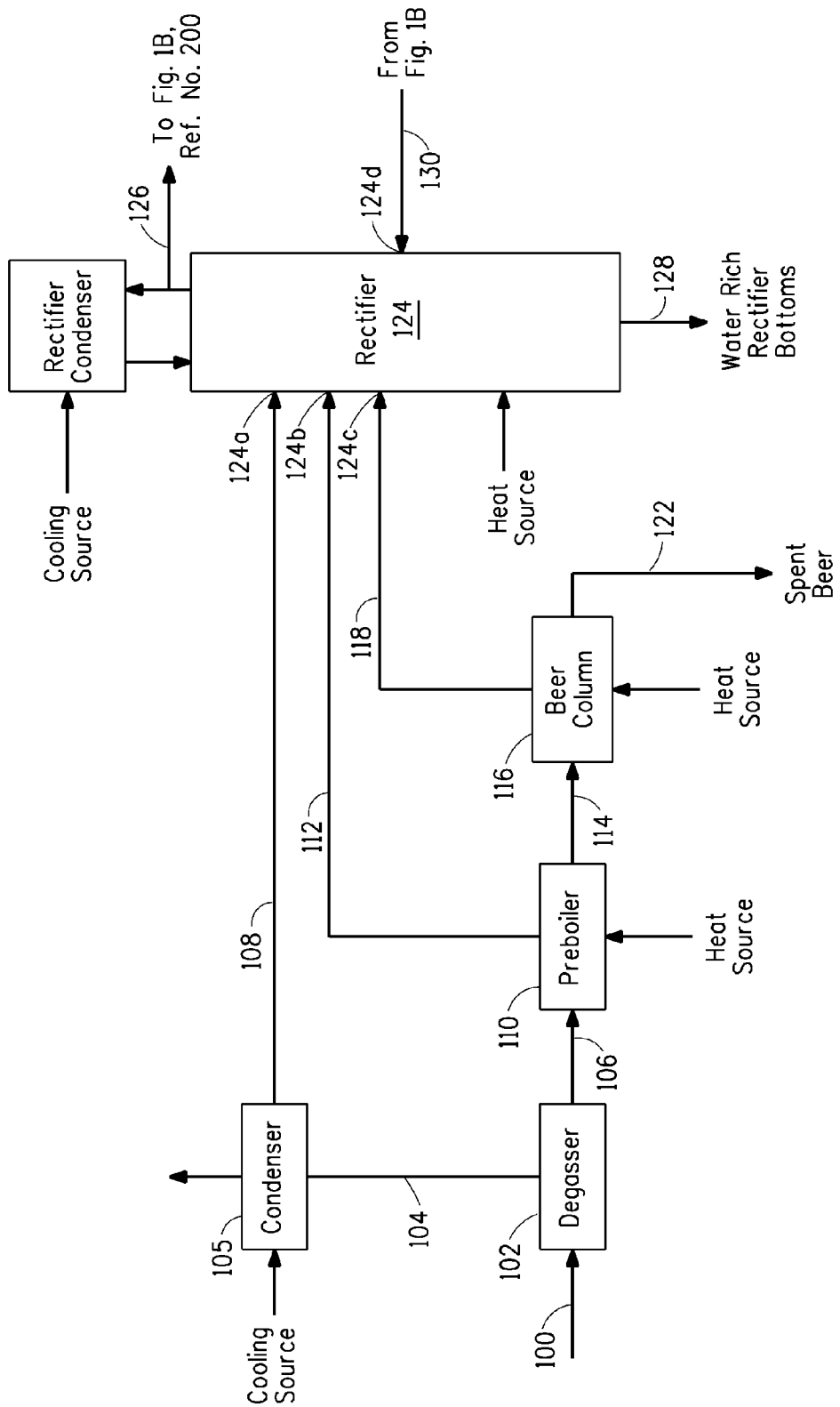
FIGS. 1A and 1B illustrate a system useful for practicing the invention including a pre-boiler 110 providing a vapor by-pass fraction.
Figure 1B:
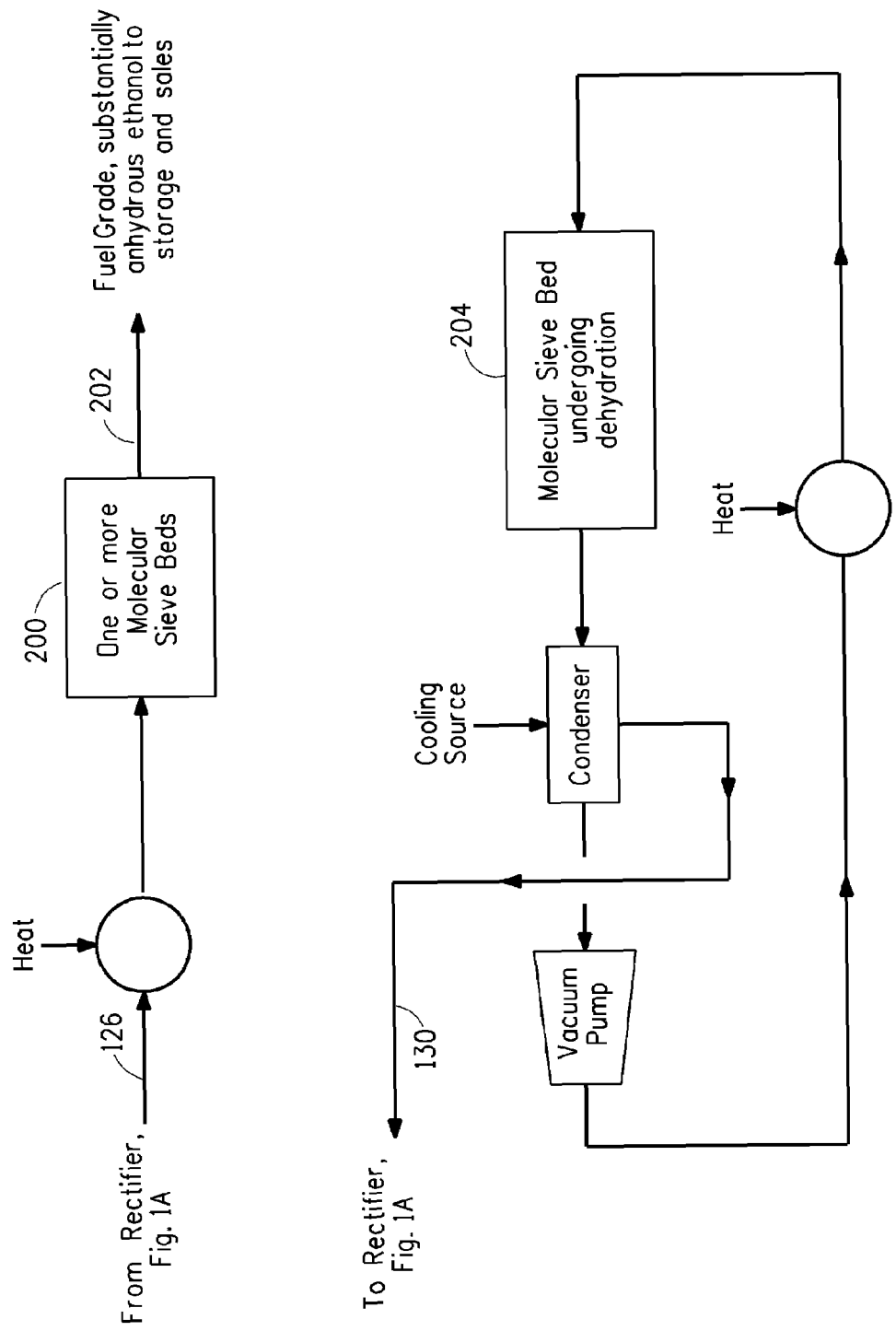

The process of the invention can be understood by referring to FIG. 1, which illustrates a system useful for practicing the invention. The beer stream 100 first is degassed to remove a substantial portion of the carbon dioxide in a degasser 102. This can be accomplished by any of the known methods available including: applying a vacuum or heating to a boil. The carbon dioxide stream 104 can be partially condensed in a condenser 105 to produce a degasser condensate stream 108 that can be returned to the process stream at various points, such as the beer column 116, or preferably, to the rectifier column 124 at a first feed point 124a.

The degassed beer feed 106 is passed to a pre-boiler 110 in which the degassed beer feed is heated sufficiently to flash a portion of the ethanol-water mix to provide a vapor by-pass fraction 112, rich in ethanol, and a beer column feed fraction 114. The pre-boiler 110 includes an inlet, beer column feed outlet communicating with said beer column 116, a vapor-by-pass outlet communicating with a rectifier column 124, and a heating means. The pre-boiler 110 can be a heated tank, an evaporation pan, a heated surface, a shell-and-tube heat exchanger with vapor disengagement space, or a wiped film evaporator and the like. Preferably the pre-boiler has a means to avoid build-up of solids.

The vapor-by-pass fraction 112 can include about 2 to about 14 wt % and preferably, about 4 to about 12 wt %, of the degassed beer feed and comprises about 30 to about 60 wt % ethanol, preferably about 40 to about 50 wt %. The vapor by-pass fraction 112 communicates directly with the rectifier 124 at a second feed point 124b in a preferred embodiment. First and second feed points 124a and 124b can be the same or different.

The beer column feed fraction 114 communicates with the beer column 116, where it is distilled to provide an overhead vapor fraction 118 communicating with the rectifier column 124 at a third feed point 124c and a spent beer fraction 122. The beer column 116 can be any conventional column useful for stripping ethanol from aqueous phases and includes, a beer column feed inlet, an overhead vapor outlet, a spent beer fraction outlet, a heating means and includes multiple fractionation trays.

The overhead vapor fraction 118 is an ethanol-water vapor stream that includes substantially all the ethanol present in the beer column feed fraction 114. The ethanol remaining in the spent beer fraction 122 is usually less than 0.1 wt %. The spent beer stream may be dewatered and the solids processed for livestock feeds or other purposes.

The overhead vapor fraction 118 and the vapor-by-pass fraction 112 are distilled in the rectifier column 124 to provide an ethanol-rich rectifier overhead vapor stream 126 and a water-rich rectifier bottoms stream 128. The rectifier column (124) can be any conventional column useful for distilling ethanol and includes at least two feed points 124b and 124c for vapor streams, an overhead vapor outlet, a rectifier bottoms outlet, a heating means, a partial condenser, and a series of fractionation trays. Preferably, the rectifier column has a larger diameter above the third feed point 124c, for the overhead vapor stream; and second feed point 124b for the vapor by-pass fraction deposed at or above the second feed point 124c.

The rectifier overhead vapor stream 126, comprising about 80 to about 95 wt % ethanol, preferably about 90 to about 94 wt % ethanol, and the remainder, substantially water, can be processed further to remove water and increase the purity of the ethanol, ultimately to achieve about a 99.5 wt % ethanol stream which is fuel-grade ethanol. For instance, the rectifier over-head vapor stream 126 can be passed through one or more molecular sieve beds 200, as illustrated in FIG. 1, to remove a substantial portion of the residual water and provide a fuel-grade anhydrous ethanol stream 202. This process, and variations thereof, using a variety of dehydrating materials and methods are well known. For instance, Aden et al., (2002), describes the use of 3 A molecular sieves as the dehydrating agent; Ladisch et al., (I&EC Process Design & Development, 1984, 23, p. 437) describes the use of corn grits dehydrating agent; and U.S. Pat. No. 4,983,304 discloses membranes useful in separation of ethanol from water. In this process the molecular sieve beds can be regenerated offline by a number of conventional processes such as passing hot gas, for instance carbon dioxide, through the bed as disclosed in BR 8703445(A1); or by passing anhydrous ethanol through the bed as disclosed in Aden (2002). Preferably, the above referenced dehydration processes provide a regenerate stream 130 comprising an ethanol-water mix that is fed back to the rectifier column 124 at a fourth feed point 124d. The regenerate stream can include about 1 to about 90 wt % ethanol and can consume about 1 to up to about 40% column capacity of the rectifier column.

In existing processes where the size of the rectifier 124 is fixed, the overall throughput of the system is dependent upon the quantity and composition of the regenerate stream, among other variables. Dehydration methods that act to decrease the volume of ethanol in the regenerate stream 130 should free capacity in the rectifier column 124. In concept, beer columns could be run at higher throughput to fill the free capacity; and thus, improve the throughput of the system. However, in many existing systems, the beer column and rectifier columns are designed to have equivalent capacities. If free capacity is available in the rectifier column, the beer column cannot match the rectifier column throughput if it is already running at capacity. Thus, the beer column can become a bottleneck for the system. The process of the invention, wherein a vapor bypass fraction 112 by-passes the beer column, can be used to shift burden to the rectifier column 124. Specific further embodiments of the invention including preferred dehydration methods; preferred condensation, or partial condensation, of the vapor by-pass fraction 112; and partial condensation of the overhead vapor fraction 118 are described below.

Figure 2:
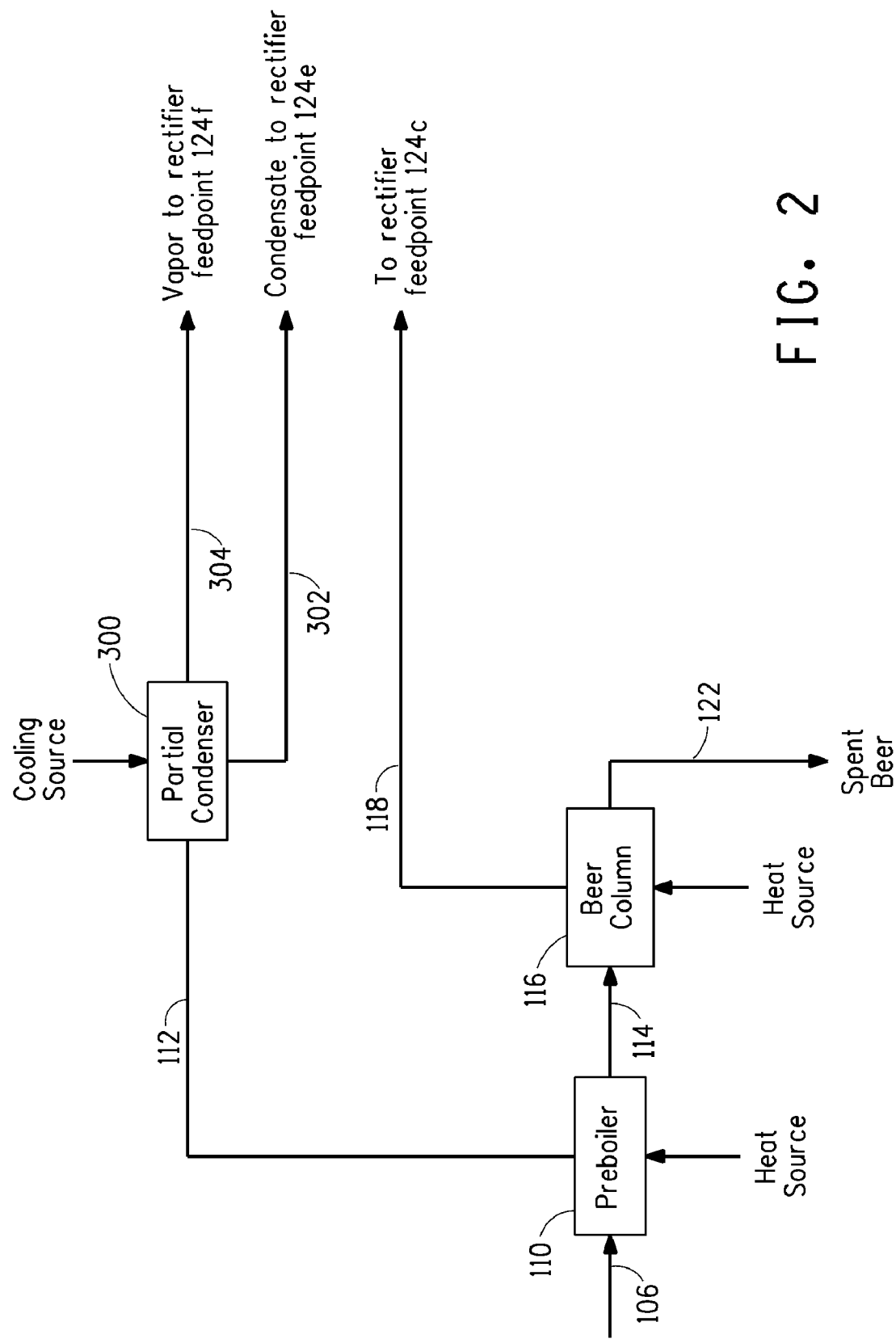
FIG. 2 illustrates a system useful for practicing the invention including a condenser 300 for partial or total condensation of the vapor by-pass fraction 112.

Another embodiment of the invention is illustrated in FIG. 2, wherein the vapor by-pass fraction 112 is partially or totally condensed, with a condenser 300 to provide: a vapor by-pass condensate fraction 302 communicating at a fifth feed point 124e with the rectifier column 124; and a remaining vapor by-pass stream 304 communicating with the rectifier column 124 at a sixth feed point 124f. Preferably the vapor by-pass condensate fraction 302 is about 40 to 100 wt % of the vapor by-pass fraction.

Figure 3:
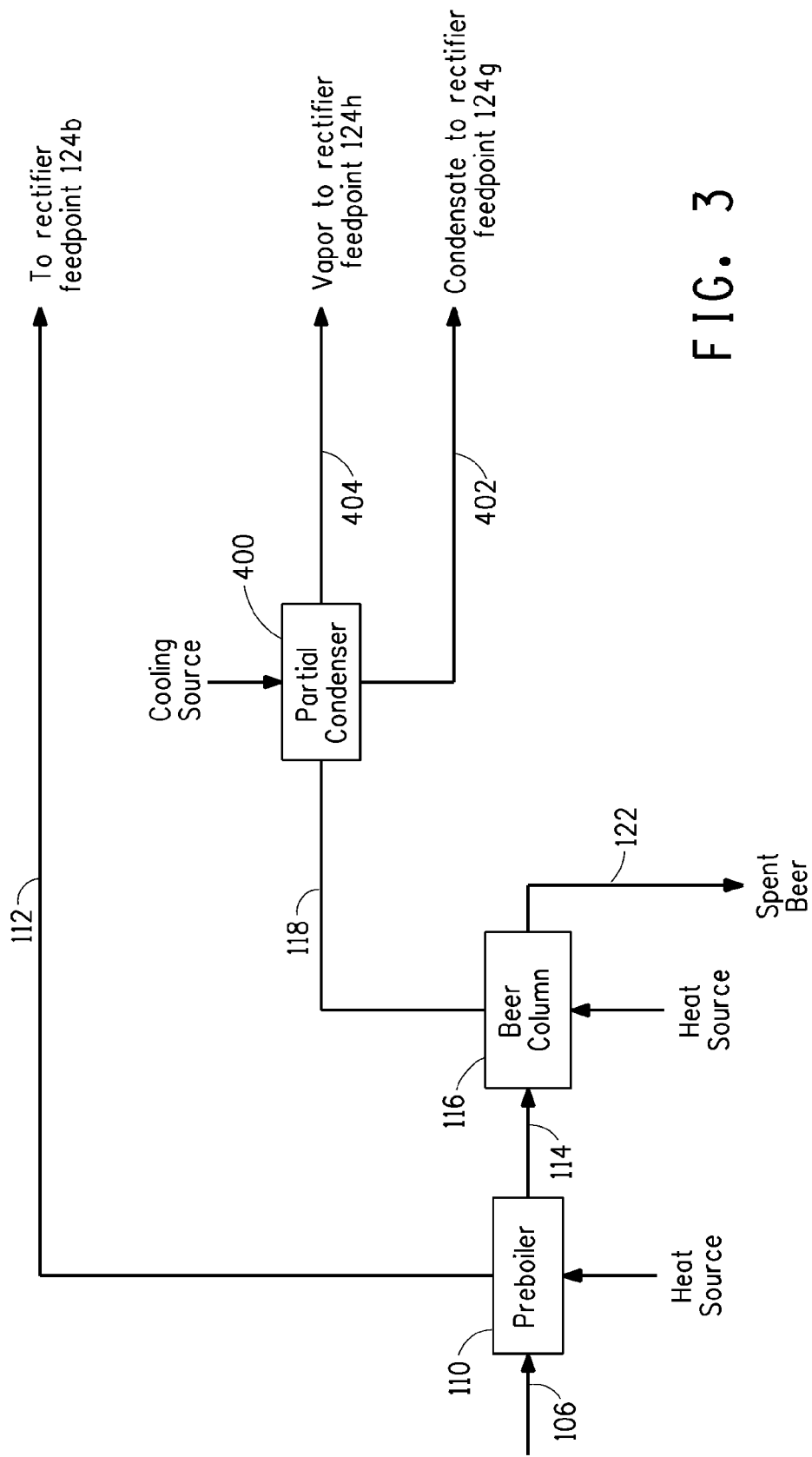
FIG. 3 illustrates a system useful for practicing the invention including a condenser 400 for partial condensation of the overhead vapor fraction 118.

Another embodiment of the invention is illustrated in FIG. 3, wherein the over-head vapor fraction 118 is partially condensed with a condenser 400 to provide: an overhead vapor condensate fraction 402 communicating with the rectifier column 124 at a seventh feed point 124g; and a remaining overhead vapor stream 404 communicating with the rectifier column 124 at an eighth feed point 124h. Preferably the overhead vapor condensate fraction 402 is about 5 to about 30 wt % of the overhead vapor fraction. This embodiment can be further practiced including other embodiments disclosed above.

Figure 4:
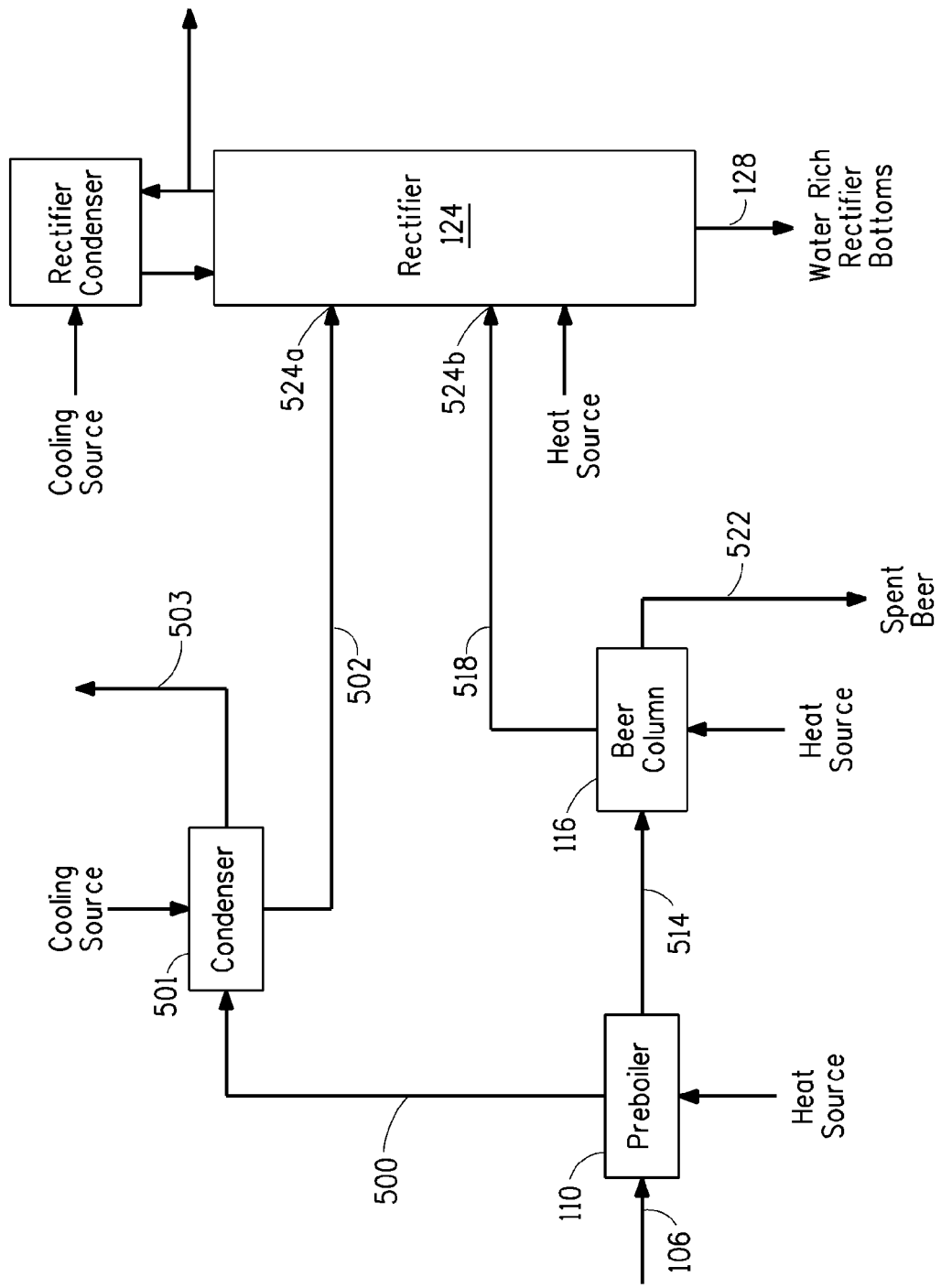
FIG. 4 illustrates a system useful for practicing the invention including a condenser 501 for partial condensation of the overhead vapor fraction 518.

Another embodiment of the invention is illustrated in FIG. 4, wherein the a beer stream comprising a liquid-solids fraction is flashed and boiled to provide a carbon dioxide-ethanol-water vapor stream 500 comprising about 2 to about 14 wt % and preferably, about 4 to about 12 wt %, of the liquid-solids fraction; and a beer column feed stream 514. The carbon dioxide-ethanol-water vapor fraction 500 is condensed with a condenser 501 to provide an ethanol-water liquid stream 502 and a carbon dioxide gas stream 503. The beer column feed stream 514 communicates with the beer column 116, where it is distilled to provide an overhead vapor fraction 518 and a spent beer fraction 522. The ethanol-water liquid stream 502 and the overhead vapor fraction 518 communicate with a rectifier column at a first feed point 524a and a second feed point 524b, respectively. The combination of ethanol-water liquid stream 502 and the overhead vapor fraction 518 is distilled in the rectifier column to provide an ethanol-rich rectifier overhead vapor stream 126 and a water-rich bottoms stream 128. This embodiment can be further practiced including other embodiments disclosed above.

Figure 5:
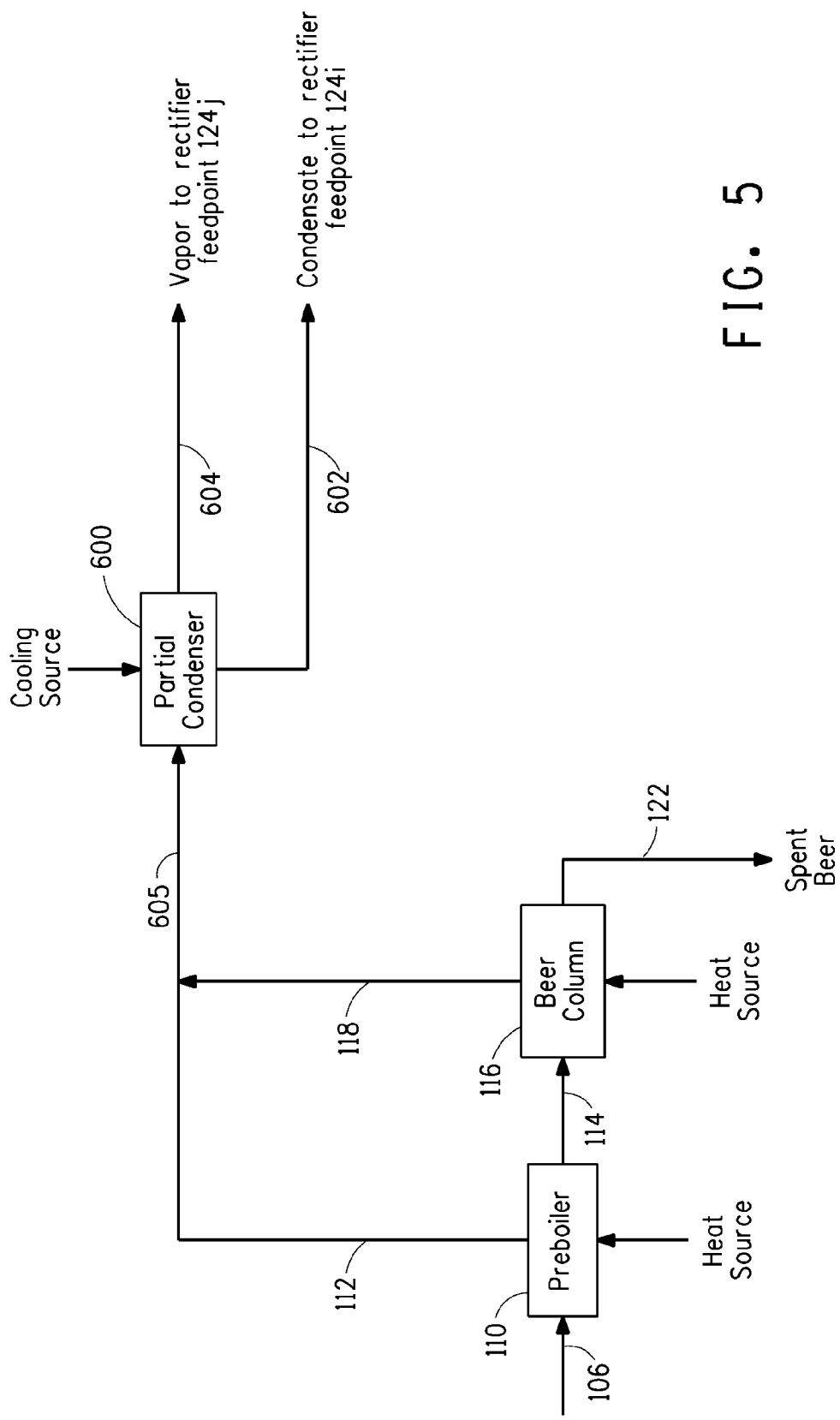
FIG. 5 illustrates a system useful for practicing the invention including a condenser 600 for partial condensation of the total vapor stream 605.

In another embodiment of the invention, illustrated in FIG. 5, the overhead vapor fraction 118 and the vapor-by-pass fraction 112 are combined to provide a total vapor stream 605 that is partially condensed with a condenser 600 to provide a total ethanol-water condensate fraction 602 and a remaining total vapor stream 604. The total ethanol-water condensate fraction 602 and the remaining total vapor stream 604 communicate with the rectifier column at ninth feed point 124i and tenth feed points 124j, respectively. The combination of the total ethanol-water condensate fraction 602 and the remaining total vapor stream 604 is distilled in the rectifier column to provide an ethanol-rich rectifier overhead vapor stream 126 and a water-rich bottoms stream 128. This embodiment can be further practiced including other embodiments disclosed above.

The process of the invention can be demonstrated using a computational model of the process. Process modeling is an established methodology used by engineers to simulate complex chemical processes. Process modeling software performs many fundamental engineering calculations, for example mass and energy balances, vapor/liquid equilibrium and reaction rate computations. The modeling of distillation columns is particularity well established. Calculations based on experimentally determined binary vapor/liquid equilibrium data can predict reliably the behavior of multi-component mixtures. This capability has been expanded to allow modeling of complex multi-stage, multi-component distillation columns using rigorous algorithms like the "inside-out" algorithm developed by Joseph Boston of Aspentech, Inc. of Cambridge, Mass. Commercial modeling software, such as Aspen Plus® from Aspentech, can be used in conjunction with physical property databases, such as DIPPR, available from the American Institute of Chemical Engineers, Inc., of New York, N.Y., to develop accurate models and assessments of processes.

The parameters inputted for the various embodiments of a conventional process and the processes of the invention are listed in Table 1.

TABLE 1

Model Inputs [a]

| Element | Variable | units |
|---|---|---|
| degassed beer feed | feedrat | lb/hr |
|  | composition | wt % |
| degasser condensate stream | feedrat | lb/hr |
|  | compositions | wt % |
| pre-boiler | vapor by-pass fraction (112) (b) | wt % |
|  | pressure in the pre-boiler | psia |
| condenser | vapor by-pass condensate fraction (302) | wt % |
| beer Column | number of theoretical stages including the column |  |
|  | top | psia |
|  | bottom | psia |
|  | feed stage |  |
|  |   degassed beer feed (106) 116a |  |
|  |   degasser condensate stream (108) 116b |  |
|  | mass fraction ethanol in bottom | wt ppm |
|  | tray details |  |
|  |   types of tray |  |
|  |   tray spacing | ft |
|  |   approach to | % |
| rectifier Column | number of stages including reboiler and column |  |
|  | top | psia |
|  | bottom | psia |

TABLE 1-continued

Model Inputs [a]

| Element | Variable | units |
|---|---|---|
| | temperature of subcooled feed stage | °F. |
| | overhead vapor fraction feedpoint | |
| | remaining overhead vapor stream (404) feedpoint | |
| | overhead vapor condensate fraction (402) feedpoint | |
| | degasser condensate stream (108) feedpoint | |
| | vapor bypass fraction (112) feedpoint | |
| | remaining vapor by-pass stream (304) feedpoint | |
| | vapor bypass condensate fraction (302) feedpoint | |
| | regenerate stream (130) feedpoint | |
| | ethanol concentration in rectifier bottoms stream | wt ppm |
| | ethanol concentration in rectifier over-head vapor stream | wt % |
| | tray details (upper) | |
| | types of tray | |
| | tray spacing | ft |
| | approach to | % |
| | tray details (lower) | |
| | types of tray | |
| | tray spacing | ft |
| | approach to | % |
| molecular sieve superheater | outlet | °F. |
| molecular sieve beds | time averaged flowrate of component exiting with regenerate stream (130)/average of the same in rectifier overhead vapor stream | |
| | component | % |
| | component | % |
| | regenerate stream (130) | °F. |

(a) Does not include physical property parameters and modeling inputs related to convergence and other computational options or diagnostics.

(b) The vapor by-pass fraction is expressed in terms of the wt % of the degassed beer feed vaporized, based on the total weight of the degassed beer feed 106.

Table 2 lists typical feed compositions for the ethanol refining area of a dry grind fuel ethanol plant. These compositions were used in modeling a conventional process and the processes of the invention.

TABLE 2

Feed Compositions compositions expressed as wt fractions

| | | |
|---|---|---|
| degassed beer feed (106) | water | 79.88% |
| | ethanol | 9.29% |
| | glucose | 0.00% |
| | non-fermentable dissolved solids | 4.05% |
| | xylose | 0.00% |
| | soluable proteins | 1.53% |
| | starch | 0.18% |
| | arabinose | 1.38% |
| | galactose + mannose | 0.79% |
| | insoluable proteins | 1.83% |
| | oil | 1.06% |
| | CO2 | 0.005% |
| degasser condensate stream (108) | water | 47.87% |
| | ethanol | 51.79% |
| | CO2 | 0.34% |

The model was used to predict the capacity of an ethanol refining area using the various embodiments of this invention.

Capacity of the ethanol purification area in an existing plant is commonly established by one or more equipment limitations or bottlenecks. Common bottlenecks include the column diameters, and the reboiler and condenser capacities. If internal flows in a distillation column exceed the maximum allowable rates, flooding will occur and separation efficiency will degrade quickly. In this situation, capacity is limited by the diameter of the existing column. Likewise, if required, reboiler duties are greater than what can be achieved with the existing equipment; capacity will be limited by that resource. Similarly, the condensers can be limiting. The modeling described herein has studied the column diameter limitations, knowing that modifications which impact flooding in the lower part of the column have an equivalent impact on reboiler capacity. Likewise, modifications that impact flooding in the upper part of the column have an equivalent impact on the condenser capacity.

Figure 6A:
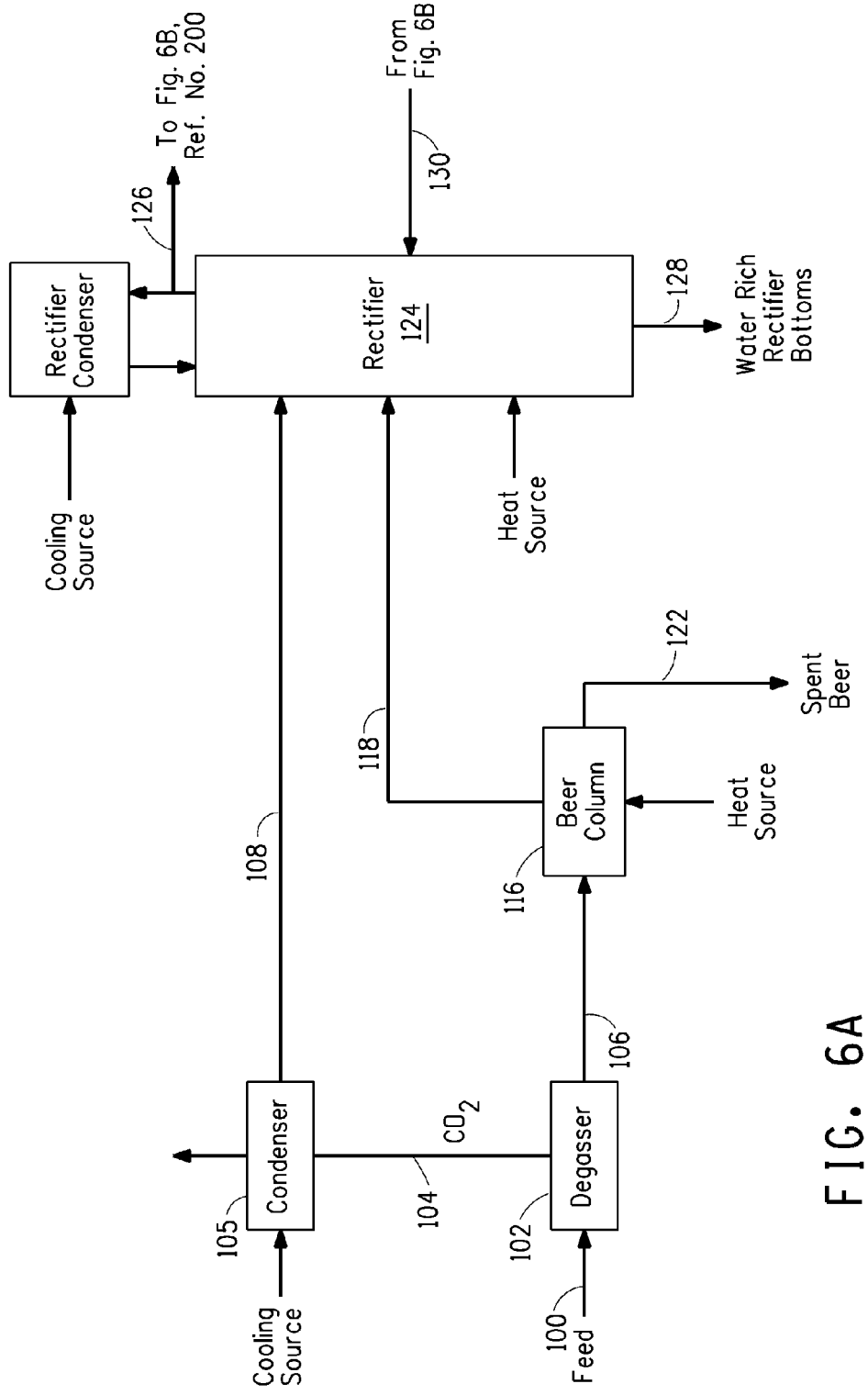
FIGS. 6A and 6B illustrate a conventional, prior art system as a comparison.
Figure 6B:
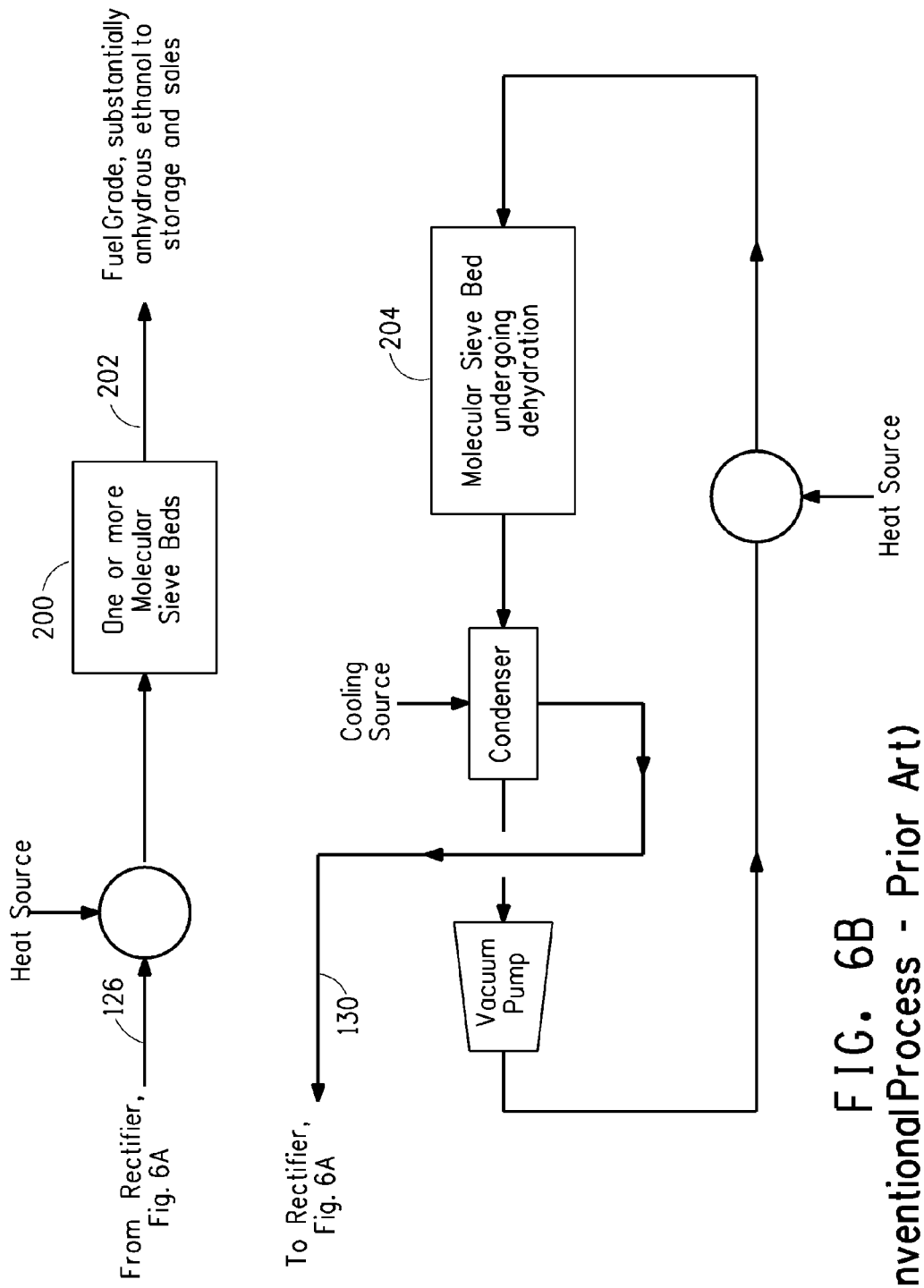

Benchmark values for potential capacity bottlenecks were established by a simulation of a conventional commercial dry grind facility producing 25 MM gal/year of ethanol, and using 99.5% ethanol vapor for the molecular sieve regeneration process. It was assumed that the capacity of the process represented by that simulation was simultaneously limited by beer column diameter and rectifier column diameters (upper and lower sections). The conditions used in the simulation for this conventional process are listed as Case A in Table 3 and follow a conventional process as outlined in FIG. 6.

TABLE 3

|  |  | Case A | units |
|---|---|---|---|
| Inputs | | | |
| degassed beer feed (106) | feedrate | 194726 | lb/hr |
| degasser condensate stream (108) | feedrate | 1578 | lb/hr |
| beer Column (116) | number of theoritical stages including the reboiler | 9 | |
|  | column pressures | | |
|  | top | 22 | psia |
|  | bottom | 24.2 | psia |
|  | feed stage locations | | |
|  | degassed beer feed (106) feedpoint 116a | 1 | |
|  | degasser condensate stream (108) feedpoint 116b | 1 | |
|  | mass fraction ethanol in bottom product | 500 | wt ppm |
|  | tray details | | |
|  | types of tray | sieve | |
|  | tray spacing | 2 | ft |
|  | approach to flood | 61.75 | % |
| rectifier Column (124) | number of stages including reboiler and condenser | 18 | |
|  | column pressures | | |
|  | top | 20 | psia |
|  | bottom | 24 | psia |
|  | temperature of subcooled reflux | 175 | °F. |
|  | feed stage locations | | |
|  | overhead vapor fraction (118) feedpoint 124c | 9 | |
|  | regenerate stream (130) feedpoint 124d | 7 | |
|  | ethanol concentration in rectifier bottoms stream (128) | 500 | wt ppm |
|  | ethanol concentration in rectifier over-head vapor stream (126) | 90.85 | wt % |
|  | tray details (upper section) | | |
|  | types of tray | sieve | |
|  | tray spacing | 2 | ft |
|  | approach to flood | 61.75 | % |
|  | tray details (lower section) | | |
|  | types of tray | sieve | |
|  | tray spacing | 2 | ft |
|  | approach to flood | 50 | % |
| molecular sieve superheater | outlet temperature | 240 | °F. |
| molecular sieve beds (200) | time averaged flowrate of component exiting with regenerate stream (130)/average flowrate of the same component in rectifier overhead vapor stream (126) | | |
|  | component water | 96.78 | % |
|  | component ethanol | 16.22 | % |
|  | regenerate stream (130) temperature | 176 | °F. |
| Outputs | | | |
|  | production rate of fuel grade anhydrous ethanol (202) | 19849 | lb/hr |
|  | required beer column diameter | 6.82 | ft |
|  | required rectifier column upper section diameter | 8.07 | ft |
|  | required rectifier column lower section diameter | 4.43 | ft |

This simulation established the set of benchmark bottlenecks listed in Table 4. These values were used to quantify the potential benefits of the invention in the context of specific examples.

TABLE 4

Benchmark Bottlenecks

| Beer Column Diameter | 6.82 ft |
|---|---|
| Rectifier Column Upper Diameter | 8.07 ft |
| Rectifier Column Lower Diameter | 4.43 ft |

In a second conventional simulation, Case B, all the assumptions and inputs of Case A were used with the exceptions that regeneration of the molecular sieve bed 200 was carried out with a hot, inert gas, for example carbon dioxide, as disclosed in BR 8703445(A1); and the resulting regenerate stream 130 was fed to the rectifier column at about 95° F. The potential capacity gains from this modification, relative to Case A, are shown in Table 5.

TABLE 5

| Capacity increase when bottleneck is located in: | case B | units |
|---|---|---|
| the beer column or reboiler | 0 | % |
| upper section of the rectifier column or condenser | 9.1 | % |
| lower section of the rectifier column or reboiler | 78.2 | % |

This modification would increase overall capacity in plants where the Rectifier column is the bottleneck and there is excess capacity in the Beer Column. But in plants where the beer column limits capacity, rates could not be increased because there is no mechanism for balancing capacity load between the beer column 116 and rectifier column 124. Process throughput could only be increased if there was excess capacity in the beer column 116.

Five cases were run to demonstrate the benefits of the invention. For each case, a particular modification was made to the simulated process, and then four independent simulations were done to quantify the potential impact of the modification. In each of the independent simulations, the feeds were increased until one specific bottleneck reached its benchmark value. By comparing the resulting capacity achieved with the modified process to the benchmark established in case A, the impact of the modification on each particular bottleneck was quantified. In an actual plant, one specific bottleneck will generally limit capacity. A modification that positively impacts a particular bottleneck will increase total capacity.

In the examples of the invention, modifications were made to the model used in case B. Results are shown in Table 6:

(a) The vapor by-pass fraction is expressed in terms of the wt % of the degassed beer feed vaporized, based on the total weight of the degassed beer feed 106.

The impacts of key process parameters including: 1) the vapor by-pass fraction wt % provided by flashing of the degassed beer feed 106 in the pre-boiler 110; 2) the amount of vapor by pass fraction 112 condensed; and 3) the feed location of the resulting vapor and liquid feeds to the rectifier column 124, were explored. These cases demonstrate that the

TABLE 6

| | | Examples | | | | | |
| --- | --- | --- | --- | --- | --- | --- | --- |
| | | 1 | 2 | 3 | 4 | 5 | units |
| | Inputs | | | | | | |
| pre-boiler (110) | vapor by-pass fraction (112) (a) | 4.75 | 9.12 | 4.75 | 9.12 | 2.78 | wt % |
| | pressure maintained in the pre-boiler | 23.5 | 23.5 | 23.5 | 23.5 | 23.5 | psia |
| condenser (300) | vapor by-pass condensate fraction (302) | 0 | 0 | 40.6 | 40.6 | 100 | wt % |
| beer column (116) | number of theoretical stages including the reboiler | 9 | 9 | 9 | 9 | 9 | |
| | column pressures | | | | | | |
| | top | 22 | 22 | 22 | 22 | 22 | psia |
| | bottom | 24.2 | 24.2 | 24.2 | 24.2 | 24.2 | psia |
| | feed stage locations | | | | | | |
| | degassed beer feed (106) feedpoint 116a | 1 | 1 | 1 | 1 | 1 | |
| | mass fraction ethanol in bottom product | 500 | 500 | 500 | 500 | 500 | wt ppm |
| | tray details | | | | | | |
| | types of tray | sieve | sieve | sieve | sieve | sieve | |
| | tray spacing | 2 | 2 | 2 | 2 | 2 | ft |
| | approach to flood | 61.75 | 61.75 | 61.75 | 61.75 | 61.75 | % |
| rectifier column (124) | number of stages including reboiler and condenser | 18 | 18 | 18 | 18 | 18 | |
| | column pressures | | | | | | |
| | top | 20 | 20 | 20 | 20 | 20 | psia |
| | bottom | 24 | 24 | 24 | 24 | 24 | psia |
| | temperature of subcooled reflux | 175 | 175 | 175 | 175 | 175 | ° F. |
| | feed stage locations | | | | | | |
| | overhead vapor fraction (118) feedpoint 124c | 9 | 9 | 9 | 9 | 9 | |
| | degasser condensate stream (108) feedpoint 124a | 8 | 8 | 8 | 8 | 8 | |
| | remaining vapor by-pass stream (304) feedpoint 124f | 9 | 9 | 9 | 9 | — | |
| | vapor bypass condensate fraction (302) feedpoint 124e | — | — | 14 | 14 | 8 | |
| | regenerate stream (130) feedpoint 124d | 18 | 18 | 18 | 18 | 18 | |
| | ethanol concentration in rectifier bottoms stream (128) | 500 | 500 | 500 | 500 | 500 | wt ppm |
| | ethanol concentration in rectifier over-head vapor stream (126) | 90.85 | 90.85 | 90.85 | 90.85 | 90.85 | wt % |
| | tray details (upper section) | | | | | | |
| | types of tray | sieve | sieve | sieve | sieve | sieve | |
| | tray spacing | 2 | 2 | 2 | 2 | 2 | ft |
| | approach to flood | 61.75 | 61.75 | 61.75 | 61.75 | 61.75 | % |
| | tray details (lower section) | | | | | | |
| | types of tray | sieve | sieve | sieve | sieve | sieve | |
| | tray spacing | 2 | 2 | 2 | 2 | 2 | ft |
| | approach to flood | 50 | 50 | 50 | 50 | 50 | % |
| molecular sieve superheater | outlet temperature | 240 | 240 | 240 | 240 | 240 | ° F. |
| molecular sieve beds (200) | time averaged flowrate of component exiting with regenerate stream (130)/average flowrate of the same component in rectifier overhead vapor stream (126) | | | | | | |
| | component water | 96.78 | 96.78 | 96.78 | 96.78 | 96.78 | % |
| | component ethanol | 0 | 0 | 0 | 0 | 0 | % |
| | regenerate stream (130) temperature | 95 | 95 | 95 | 95 | 95 | ° F. |
| | Outputs | | | | | | |
| | Capacity increase when bottleneck is located in: | | | | | | |
| | the beer column or reboiler | 14.7 | 25.7 | 14.7 | 25.7 | 10 | % |
| | upper section of the rectifier column or condenser | −3 | −14.8 | 3.8 | −2.8 | 10.4 | % |
| | lower section of the rectifier column or reboiler | 108 | 104 | 71.7 | 52.7 | 44.2 | % | embodiments of the invention can be utilized to increase the overall capacity of the ethanol recovery area of a dry grind plant, and they show how a particular plant might be balanced and optimized by adjusting key process parameters.

All the examples described below use a hot inert gas for regeneration of molecular sieve beds 200. However, the advantages of the processes of the invention can be realized with conventional regeneration processes, for instance using 99.5% ethanol vapor. This advantage is achieved when any system is limited by the beer column and has extra capacity in the rectifier column, and in particular, in the upper section of the rectifier column.

EXAMPLE 1

In this Example, the degassed beer feed 106 is flashed in the pre-boiler 110 to provide a vapor by-pass fraction 112 of 4.75 wt % that is fed to the rectifier column 124 at second feed point 124*b*. Feed point 124*b* in this example corresponds to stage 9 of the 18 stages comprising the rectifier column. Further, the beer column is limiting and there is extra capacity in the upper section of the rectifier column. As shown in Table 6, overall capacity can be increased by 14.7%.

EXAMPLE 2

In this Example, the degassed beer feed 106 is flashed in the pre-boiler 110 to provide a vapor by-pass fraction 112 of 9.12 wt % that is fed to the rectifier column 124 at second feed point 124*b*. Feed point 124*b* in this example corresponds to stage 9 of the 18 stages comprising the rectifier column. Also, the beer column is limiting and there is sufficient extra capacity in the upper section of the rectifier column. As shown in Table 6, if the overall capacity can be increased by 25.7%.

EXAMPLE 3

In this Example, Example 1 is repeated, except that the vapor bypass fraction 112 of 4.75 wt % is partially condensed to provide a vapor by-pass condensate fraction of 40.6 wt % that is fed to the rectifier column 124 at fifth feed point 124*e*. Feed point 124*e* in this Example corresponds to stage 14 of the 18 stages comprising the rectifier column. The remaining vapor by-pass stream 304 is fed to the rectifier column 124 at sixth feed point 124*f* at stage 9. The beer column is the bottleneck in this Example. This combination of parameters results in an overall capacity increase of 14.7%. Capacity of the upper section of the rectifier column is also increased. If the upper section of the rectifier column is limiting, overall capacity is increased by 3.8%.

EXAMPLE 4

In this Example, the degassed beer feed 106 is flashed in the pre-boiler 110 to provide a vapor by-pass fraction 112 of 9.12 wt % that is partially condensed to provide a vapor by-pass condensate fraction of 40.6 wt % that is fed to the rectifier column 124 at fifth feed point 124*e*. Feed point 124*e* in this example corresponds to stage 14 of the 18 stages comprising the rectifier column. The remaining vapor by-pass stream 304 is fed to the rectifier column 124 at sixth feed point 124*f* at stage 9. In this Example, the beer column is limiting and there is sufficient extra capacity in the upper section of the rectifier column. This combination of parameters results in an overall of 25.7%.

EXAMPLE 5

In this Example, the degassed beer feed 106 is flashed in the pre-boiler 110 to provide a vapor by-pass fraction 112 of 2.78 wt %, that is fully condensed to provide a vapor by-pass condensate fraction of 100 wt % that is fed to the rectifier column 124 at fifth feed point 124*e*. Feed point 124*e* in this example corresponds to stage 8 of the 18 stages comprising the rectifier column. This Example generates equivalent capacity increases in both the beer and rectifier columns. It shows that a 10% increase in overall capacity can be achieved when both the beer column and upper section of the rectifier column are near their capacity limits.

We claim:
1. A process for providing ethanol comprising:
  a) flashing carbon dioxide from a beer stream (100) to provide a carbon dioxide gas stream (104) and a degassed beer feed (106);
  b) boiling the degassed beer feed (106) in a pre-boiler (110) to provide a vapor by-pass fraction (112) and a beer column feed stream (114);
  c) distilling the beer column feed stream (114) in a beer column to provide an overhead vapor fraction (118) and a spent beer fraction (122);
  d) distilling in a rectifier column (124), a combination comprising the vapor by-pass fraction (112) and the overhead vapor fraction (118) to provide an ethanol-rich rectifier overhead vapor stream (126) and a water-rich rectifier bottoms stream (128).

2. The process of claim 1, further comprising:
  e) cooling the carbon dioxide gas stream (104) with a first condenser (105) to provide a degasser condensate stream (108);
wherein in step (d) distilling, said combination further comprises the degasser condensate stream (108).

3. The process of claim 2 further comprising:
  f) condensing the vapor by-pass fraction to provide a vapor by-pass condensate fraction (302) and a remaining vapor by-pass stream (304);
wherein in step (d) distilling, said combination further comprises the vapor by-pass condensate fraction and the remaining vapor by-pass stream.

4. The process of claim 3 further comprising:
  g) condensing a portion of the overhead vapor fraction to provide an overhead vapor condensate fraction (402) and a remaining vapor overhead fraction (404);
wherein in step (d) distilling, said combination further comprises the overhead vapor condensate fraction (402) and the remaining vapor overhead fraction (404).

5. The process of claims 1, 3 or 4, further comprising:
  (i) dehydrating said rectifier overhead vapor stream (126) by passing the stream through one or more active molecular sieve beds (200) to provide an anhydrous ethanol vapor stream (202) and one or more water-rich molecular sieve beds;
  (ii) dehydrating the water-rich molecular sieve bed (204) to provide an active molecular sieve bed and a regenerate ethanol-water stream (130); and
  (iii) providing to the rectifier column the regenerate ethanol-water stream (130);
wherein in step (d) distilling, said combination further comprises the regenerate ethanol-water stream (130).

6. The process of claim 5, wherein the rectifier column further comprises:
- a first feed point (124a) for the degasser condensate stream (108);
- a second feed point (124b) for the vapor by-pass fraction (112);
- a third feed point (124c) for the overhead vapor fraction (118);
- a fourth feed point (124d) for the regenerate ethanol-water stream (130);
- a fifth feed point (124e) for the vapor by-pass condensate fraction (302);
- a sixth feed point (124f) for the remaining vapor by-pass stream (304); and further comprises:
  - optimizing the first, second, third, fourth, fifth and sixth feed points, the vapor by-pass fraction and the vapor by-pass condensate fraction to provide an optimal throughput and energy use.

7. The process of claims 1, 3 or 4, further comprising:
- (i) dehydrating said rectifier overhead vapor stream (126) by passing the stream through one or more active molecular sieve beds (200) to provide an anhydrous ethanol vapor stream (202) and one or more water-rich molecular sieve beds;
- (ii) dehydrating the water-rich molecular sieve bed (204) to provide an active molecular sieve bed and a regenerate ethanol-water stream (130); and
- (iii) providing to the rectifier column the regenerate ethanol-water stream (130);
- wherein in step (d) distilling, said combination further comprises the regenerate ethanol-water stream (130); and wherein said step (ii) dehydrating the water-rich molecular sieve bed (204) comprises:
1. off-line, passing a dry non-condensable gas stream through the water-rich molecular sieve bed to provide a wet gas stream communicating with a condenser, and an active molecular sieve bed;
2. condensing the wet gas stream to provide said regenerate ethanol-water stream (130).

8. The process of claims 1, 3 or 4, further comprising:
- (i) dehydrating said rectifier overhead vapor stream (126) by passing the stream through one or more active molecular sieve beds (200) to provide an anhydrous ethanol vapor stream (202) and one or more water-rich molecular sieve beds;
- (ii) dehydrating the water-rich molecular sieve bed (204) to provide an active molecular sieve bed and a regenerate ethanol-water stream (130); and
- (iii) providing to the rectifier column the regenerate ethanol-water stream (130);
- wherein in step (d) distilling, said combination further comprises the regenerate ethanol-water stream (130); and wherein said step (ii) dehydrating the water-rich molecular sieve bed (204) comprises:
1. off-line, applying a vacuum through the molecular sieve bed to provide a wet vacuum stream communicating with a condenser, and an active molecular sieve bed;
2. condensing the wet vacuum stream to provide said regenerate ethanol-water stream (130).

9. The process of claim 1 wherein the vapor by-pass fraction (112) comprises 2 to 14 wt % of said degassed beer feed (106).

10. A process for providing ethanol, comprising:
- a) flashing and boiling from a beer stream comprising a liquid-solids fraction, carbon dioxide and about 2 to about 14 wt % of the liquid-solids fraction to provide a beer column feed stream (514) and a carbon dioxide-ethanol-water vapor fraction (500);
- b) condensing the carbon dioxide-ethanol-water stream to provide a ethanol-water liquid stream (502) and a carbon dioxide gas stream;
- c) distilling the beer column feed stream in a beer column to provide an overhead vapor fraction (518) and a spent beer fraction (522); and
- d) distilling, in a rectifier column (124) a combination of the ethanol-water liquid stream (502) and the overhead vapor fraction (518) to provide an ethanol-rich rectifier overhead vapor stream (126) and a water-rich rectifier bottoms stream (128).

11. The process of claim 10 wherein said ethanol-water liquid stream (502) communicates with the rectifier column (124) at a first feed point (524a) and said overhead vapor fraction (518) communicates with the rectifier column at a second feed point (524b).

12. The process of claim 11 further comprising:
- e) dehydrating said rectifier overhead vapor stream (126) by passing the stream through a series of one or more active molecular sieve beds (200) to provide an anhydrous ethanol vapor stream (202) and one or more water-rich molecular sieve beds; and
- f) dehydrating the water-rich molecular sieve bed (204) to provide an active molecular sieve bed and a regenerate ethanol-water stream (130).

13. The process of claim 12 further comprising:
- g) providing, to the rectifier column, the regenerate ethanol-water stream (130);
wherein in step (d) distilling, said combination further comprises the regenerate ethanol-water stream (130).

* * * * *

UNITED STATES PATENT AND TRADEMARK OFFICE
CERTIFICATE OF CORRECTION

PATENT NO. : 7,666,282 B2  Page 1 of 1
APPLICATION NO. : 11/320206
DATED : February 23, 2010
INVENTOR(S) : Sylvester et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1061 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,282 B2 | Page 1 of 1 |
| APPLICATION NO. | : 11/320206 | |
| DATED | : February 23, 2010 | |
| INVENTOR(S) | : Robert G Sylvester et al. | |

It is certified that error appears in the above-identified patent and that said Letters Patent is hereby corrected as shown below:

Table 1, column 6, line 3, "feedrat" should read --feedrate--
Table 1, column 6, line 5, "feedrat" should read --feedrate--
Table 1, column 6, line 10, "theoritical" should read --theoretical--
Table 1, column 6, line 21, "approach to" should read --approach to flood--
Column 6, line 26, "particularity" should read --particularly--
Table 1, column 7, line 15, "tray details (upper" should read --tray details (upper section)--
Table 1, column 7, line 18, "approach to" should read --approach to flood--
Table 1, column 7, line 19, "tray details (lower" should read --tray details (lower section)--
Table 1, column 7, line 22, "approach to" should read --approach to flood--
Table 1, column 9, line 5, "theoritical" should read --theoretical--
Table 6, line 7, "theoritical" should read --theoretical--
Column 14, line 3, "of 25.7%." should read --capacity increase of 25.7%.--
Column 14, line 28, "a spent beer fraction (122);" should read --a spent beer fraction (122); and--

Signed and Sealed this

Fourth Day of January, 2011

David J. Kappos
*Director of the United States Patent and Trademark Office*